United States Patent
Verma et al.

(10) Patent No.: US 9,119,819 B2
(45) Date of Patent: Sep. 1, 2015

(54) ORAL LIQUID COMPOSITIONS OF RHEIN OR DIACEREIN

(75) Inventors: Himanshu Verma, Ranchi (IN); Rahul Dabre, Nagpor (IN); Girish Kumar Jain, Delhi (IN)

(73) Assignee: Wockhardt Ltd., Bandra-Kurla Complex, Bandra East, Mumbai (IN)

( * ) Notice: Subject to any disclaimer, the term of this patent is extended or adjusted under 35 U.S.C. 154(b) by 541 days.

(21) Appl. No.: 12/989,966

(22) PCT Filed: Sep. 23, 2008

(86) PCT No.: PCT/IB2008/053858
§ 371 (c)(1),
(2), (4) Date: Dec. 25, 2010

(87) PCT Pub. No.: WO2009/133431
PCT Pub. Date: Nov. 5, 2009

(65) Prior Publication Data
US 2011/0166225 A1 Jul. 7, 2011

(30) Foreign Application Priority Data
Apr. 30, 2008 (IN) .......................... 952/MUM/2008

(51) Int. Cl.
A61K 31/215 (2006.01)
A61K 31/192 (2006.01)
A61P 19/02 (2006.01)
A61K 9/00 (2006.01)

(52) U.S. Cl.
CPC ............. *A61K 31/192* (2013.01); *A61K 9/0095* (2013.01)

(58) Field of Classification Search
USPC .......................................................... 424/400
See application file for complete search history.

(56) References Cited

U.S. PATENT DOCUMENTS

| | | | |
|---|---|---|---|
| 5,316,768 A | 5/1994 | Hughes et al. | |
| 6,197,818 B1 | 3/2001 | Li | |
| 6,395,300 B1 * | 5/2002 | Straub et al. | ................... 424/489 |
| 2002/0128317 A1 * | 9/2002 | Charbit et al. | ................. 514/548 |
| 2003/0157172 A1 * | 8/2003 | Lu et al. | ........................ 424/469 |

FOREIGN PATENT DOCUMENTS

| | | |
|---|---|---|
| EP | 00705601 A1 | 4/1996 |
| EP | 00809995 A1 | 12/1997 |
| EP | 01352645 A1 | 10/2003 |
| EP | 1913940 A1 | 4/2008 |
| EP | 00638540 A1 | 2/2010 |
| WO | WO9503063 A1 | 2/1995 |
| WO | WO03013473 A1 | 2/2003 |
| WO | WO 03/043602 A1 * | 5/2003 |
| WO | WO03053403 A2 | 7/2003 |

OTHER PUBLICATIONS

Brown et al. (2004). "Acceptable Analytical Practices for Dissolution Testing of Poorly Soluble Compounds". Pharmaceutical Technology: www.pharmtech.com., pp. 56-65.*

* cited by examiner

*Primary Examiner* — Anoop Singh
*Assistant Examiner* — Doan Phan
(74) *Attorney, Agent, or Firm* — Bio Intellectual Property Services LLC (Bio IPS); O. (Sam) Zaghmout

(57) ABSTRACT

The invention relates to liquid pharmaceutical compositions for oral administration comprising rhein or diacerein, or salts or esters or prodrugs thereof and processes for preparing such compositions.

6 Claims, No Drawings

ORAL LIQUID COMPOSITIONS OF RHEIN OR DIACEREIN

FIELD OF THE INVENTION

The invention relates to liquid pharmaceutical compositions for oral administration comprising rhein or diacerein, or salts or esters or prodrugs thereof and processes for preparing such compositions.

BACKGROUND OF THE INVENTION

Chemically, rhein is 9,10-dihydro-4,5-dihydroxy-9,10-dioxo-2-anthracene carboxylic acid having a structure of Formula I and diacerein is 4,5-bis(acetyloxy) 9,10-dihydro-4,5-dihydroxy-9,10-dioxo-2-anthracenecarboxylic acid having a structure of Formula II. Diacerein is widely used in the treatment of osteoarthritis and has a unique mode of action that differentiates it from non-steroidal anti-inflammatory drugs (NSAIDs) and other conventional forms of drug therapy.

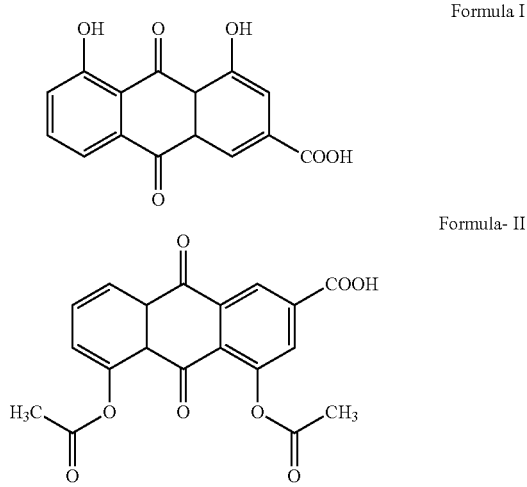

Diacerein is practically insoluble in solvents such as water, alcohols, acetone, dichloromethane and chloroform, which are generally used in pharmaceutical preparations. Although diacerein can be administered by oral route but it cannot be completely absorbed by the digestive tract, and this incomplete absorption results in undesirable side effects such as, soft stools.

In order to overcome these problems, various derivatives, pharmaceutical compositions and specific galenic forms have been proposed in the literature. For example, European patent EP 243,968 describes a diacerein potassium salt, which is water-soluble and can be used in the preparation of compositions for parenteral administration.

EP904060 discloses pharmaceutical compositions of rhein or diacerein, wherein rhein or diacerein is co-micronized with sodium lauryl sulfate.

European Patent Nos. EP263083; 264989 and 446753 disclose controlled release or delayed release compositions like multiplicity of pellets coated with drug and coating membrane or granules of drug coated with polymers or loading polymeric particles of water swellable cross-linked polymer with drug.

U.S. Pat. Nos. 5,225,192 and 5,569,469 describe different poorly soluble medicaments supported on polymeric particles of water swellable cross-linked polymer with drug.

U.S. Pat. No. 5,952,383 and European Patent No. EP 862423B1 describe pharmaceutical compositions of diacerein, rhein and their salts along with liquid support systems like oils, suspending agents, homogenizing agents and other excipients.

However, none of the formulations discussed above teach liquid oral dosage form of rhein or diacerein. Currently, diacerein is marketed as capsules in 50 mg strength under the trade name Art 50® and given twice a day. The capsule forms are, however, difficult to swallow, especially for geriatric patients. Further, the fear of swallowing, or choking on such solid shaped articles is still a concern in certain populations especially, geriatrics. It is estimated that almost 50% of the population have problems of swallowing tablets or capsules (Seager in Journal of Pharmacol. and Pharm. Pages 375-382, 1998). The capsule dosage forms become sticky when wetted by saliva, and if a patient experiences difficulty in swallowing on its first attempt, then the capsule must often be discarded. Furthermore, if a capsule partially dissolves in a patient's mouth, as can result from unsuccessful swallowing or the capsule getting stuck in the orthodontic appliance, the resulting very unpleasant taste can make it difficult to persuade the patient to take another dose. Additionally, these dosage forms are difficult to carry, store and handle. All these difficulties associated with capsules result in decreased patient compliance.

Liquid oral preparations are useful for obvious reasons. Firstly, it is preferable for patients either with physical disabilities or incapacitated. Secondly, patient compliance is often a problem with oral solid dosage forms, especially with young children and senior citizens. Thirdly, liquid compositions would help a pharmacist to dispense the correct amount of drug without resorting to sub-division of a larger dosed tablet into pieces. Fourthly, as solutions are homogenous, the medication is uniformly distributed throughout the preparation. A drug administered in solution is immediately available for absorption from the gastrointestinal tract and is more rapidly and efficiently absorbed than the same amount of drug administered in a tablet or capsule.

SUMMARY OF THE INVENTION

In one general aspect there is provided a liquid pharmaceutical composition for oral administration comprising rhein or diacerein, or salts or esters or prodrugs thereof.

The term "liquid" includes solutions, suspensions, dry syrups, syrups, elixirs, emulsions, solids ready mix that are reconstituted prior to administration Embodiments of the pharmaceutical composition may include one or more of the following features. The pharmaceutical composition may further include one or more pharmaceutically acceptable excipients. For example, the pharmaceutically acceptable excipients may include one or more of fillers, binders, lubricants, sweeteners, coloring and flavoring agents, glidants, disintegrants, and the like.

In another general aspect there is provided a process of making a liquid pharmaceutical composition for oral administration comprising rhein or diacerein, or salts or esters or prodrugs thereof, the process comprising mixing rhein or diacerein, or salts or esters or prodrugs thereof, with one or more pharmaceutically acceptable excipients.

In another general aspect there is provided a liquid pharmaceutical composition for oral administration comprising rhein or diacerein, or salts or esters or prodrugs thereof in the form of a suspension or dry syrup, wherein the composition exhibits a dissolution profile such that more than 75% of diacerein is released within 30 minutes, wherein the release rate is measured in Apparatus 2 (USP, Dissolution, paddle, 75 rpm) using 1000 ml of pH 5.7 phosphate buffer at 37° C.±0.5° C.

The details of one or more embodiments of the inventions are set forth in the description below. Other features, objects and advantages of the inventions will be apparent from the description and claims.

DETAILED DESCRIPTION OF THE INVENTION

It was a significant challenge for the inventors to obtain suitable oral liquid compositions comprising rhein or diacerein because of the insolubility of diacerein in most solvents, palatability to the patient, stability problems, especially the chemical stability of the ester in a liquid composition, wherein it is more susceptible to hydrolysis. The inventors were able to overcome this challenge and were able to develop stable oral liquid compositions comprising rhein or diacerein.

The term "liquid" includes solutions, suspensions, dry syrups, syrups, elixirs, emulsions, solids ready mix that are reconstituted prior to administration.

According to one embodiment, a liquid pharmaceutical composition comprising rhein or diacerein, or salts or esters or prodrugs thereof for oral administration may be prepared by dissolving or suspending rhein or diacerein, or salts or esters or prodrugs thereof in one or more suitable solvents to form a solution or dispersion, and optionally, adding one or more pharmaceutically acceptable excipients to the solution or dispersion of rhein or diacerein or spraying the solution or dispersion of rhein or diacerein on the pharmaceutically acceptable excipients.

According to another embodiment, a liquid pharmaceutical composition comprising rhein or diacerein, or salts or esters or prodrugs thereof for oral administration may also be prepared by directly mixing rhein or diacerein, or salts or esters or prodrugs thereof with one or more pharmaceutically acceptable excipients. This powder may be used for reconstitution prior to the administration.

The pharmaceutical acceptable excipients comprise one or more of wetting agents, solubilizers, thickening agents, sweeteners, flavoring agents, coloring agents, preservatives or buffering agents, and the like.

Suitable wetting agents or surfactants include one or more of quaternary ammonium compounds, such as benzalkonium chloride, benzethonium chloride and cetylpyridinium chloride; TPGS (d-alpha tocopheryl polyethylene glycol succinate), dioctyl sodium sulfosuccinate; polyoxyethylene alkylphenyl ethers, such as nonoxynol 9, nonoxynol 10, and octoxynol 9; poloxamers (polyoxyethylene and polyoxypropylene block copolymers); polyoxyethylene fatty acid glycerides and oils, such as polyoxyethylene (8) caprylic/capric mono- and diglycerides (e.g., Labrasol™, Gattefosse), polyoxyethylene (35) castor oil and polyoxyethylene (40) hydrogenated castor oil; polyoxyethylene alkyl ethers, such as polyoxyethylene (20) cetostearyl ether; polyoxyethylene fatty acid esters, such as polyoxyethylene (40) stearate; polyoxyethylene sorbitan esters, such as polysorbate 20 and polysorbate 80 (e.g., Tween™ 80, ICI); propylene glycol fatty acid esters, such as propylene glycol laureate (e.g., Laurogly-col™, Gattefosse); sodium lauryl sulfate; fatty acids and salts thereof, such as oleic acid, sodium oleate and triethanolamine oleate; glyceryl fatty acid esters, for example glyceryl monostearate; sorbitan esters, such as sorbitan monolaurate, sorbitan monooleate, sorbitan monopalmitate and sorbitan monostearate; tyloxapol; lecithin; stearyl triethanolamine; laurylaminopropionic acid; and mixtures thereof.

The surfactants or wetting agents may be present from about 0.25 weight percent to about 15 weight percent of the total weight of the composition.

Thickening agents or viscosity-enhancing agents may be included to generally improve the mouth-feel of the composition and/or to help coat the lining of the gastrointestinal tract. Examples of thickening agents include acacia, alginic acid bentonite, carbomer, carboxymethylcellulose calcium or sodium, cetostearyl alcohol, methyl cellulose, ethylcellulose, glycerin, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

The thickening agents may be present from about 0.1 weight percent to 20 weight percent of the total weight of the composition.

Suitable sweeteners or sweetening agents may include one or more of monosaccharides, disaccharides and polysaccharides, e.g. xylose, ribose, glucose, mannose, galactose, fructose, sucrose, maltose, invert sugar, partially hydrolyzed starch, corn syrup solids, mannitol xylitol, D-sorbitol, erythritol, pentitol, hexitol, malitol, dihydrochalcones, monellin, steviosides or glycyrrhizin; saccharin in free acid form, soluble saccharin salts, e.g. sodium or calcium saccharin salts, cyclamate salts or acesulfame K; dipeptide based sweeteners, such as L-aspartic acid derived sweeteners, e.g. aspartame; water-soluble sweeteners derived from naturally occurring water-soluble sweeteners, e.g. sucralose; and protein based sweeteners, e.g. thaumatococcus danielli (Thaumatin I and II) and the like.

The sweetening agents may be present from about 0.05 weight percent to about 10 weight percent of the total weight of the composition.

Suitable flavoring agents may include those known to a skilled artisan, such as natural, "natural-like" and artificial flavors. These flavors may be selected from synthetic flavor oils, flavoring aromatics, oleo-resins and extracts derived from plants, leaves, flowers or fruits.

Examples of flavors may include one or more of spearmint oil, cinnamon oil, peppermint oil, clove oil, bay oil, thyme oil, cedar leaf oil, oil of nutmeg, oil of sage, oil of bitter almonds, vanilla, chocolate, coffee, cocoa and citrus oil, lemon, orange, cherry, grape, lime or grapefruit, and fruit essences, e.g. apple, pear, peach, strawberry, raspberry, cherry, plum, pineapple or apricot; mints such as peppermint (including menthol, especially levomenthol), aldehydes and esters, e.g. cinnamyl acetate, cinnamaldehyde, citral, diethylacetal, dihydrocarvyl acetate, eugenyl formate or p-methylanisol; alpha-citral (geranial) and beta-citral (neral); decanal; ethyl vanillin; piperonal (heliotropine); vanillin; alpha-amyl cinnamaldehyde; butyraldehyde; valeraldehyde; citronellal; decanal; aldehyde C-8; aldehyde C-9; aldehyde C-12; 2-ethyl butyraldehyde; hexenal, i.e. trans-2; tolyl aldehyde; veratraldehyde; 2,6-dimethyl-5-heptenal (melonal); 2-6-dimethyloctanal; 2-dodecenal, and the like.

The flavoring agents may be present from about 0.01 weight percent to about 15 weight percent, of the total weight of the composition.

The coloring agent, when included, can provide the compositions with a more aesthetic and/or distinctive appearance. Colorant agents suitable for inclusion in the present invention may include one or more water-soluble synthetic organic food additives (e.g., food dyes such as food red dye Nos. 2 and 3, food yellow dye Nos. 4 and 5 and food blue dye Nos. 1 and 2), water-insoluble lake dyes (e.g., aluminum salts of the above water-soluble synthetic organic food additives, etc.), and natural pigments (e.g., beta-carotene, chlorophyll, iron oxide red, etc.). Suitable colorants include D&C Red No. 33, FD&C Red No. 3, FD&C Red No. 40, D&C Yellow No. 10, and C Yellow No. 6.

The coloring agents may be present from about 0.001 weight percent to about 1 weight percent of the total weight of the composition.

The preservatives can be added to the compositions at levels safe for ingestion to improve storage stability Suitable preservatives may include one or more of sodium benzoate, butylated hydroxy toluene, butylated hydroxyanisole, ethylenediamine tetraacetic acid, paraoxybenzoic acid esters, chlorobutanol, benzyl alcohol, phenylethylalcohol, dehydroacetic acid, sorbic acid, benzalkonium chloride, benzethonium chloride, phenol, phenylmercuric nitrate, Thimerosal.

The preservatives may be present about 0.01 weight percent to about 5 weight percent of the total weight of the composition.

Suitable buffering agents may include, but are not limited to one or more of sodium bicarbonate, potassium bicarbonate, magnesium hydroxide, magnesium lactate, magnesium gluconate, aluminum hydroxide, aluminum hydroxide/sodium bicarbonate co precipitate, amino acids, aluminum glycinate, sodium citrate, sodium tartarate, sodium acetate, sodium carbonate, sodium polyphosphate, potassium polyphosphate, sodium pyrophosphate, potassium pyrophosphate, disodium hydrogenphosphate, dipotassium hydrogenphosphate, trisodium phosphate, tripotassium phosphate, sodium acetate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, and the like.

The buffering agents may be present from about 10 weight percent to about 80 weight percent of the total weight of the composition.

Solubilizing agents are used to facilitate more uniform dispersion of an active ingredient or other excipient that is not generally soluble in the liquid carrier. Examples of suitable solubilizing agents include gelatin, egg yolk, casein, cholesterol, acacia, tragacanth, chondrus, pectin, methyl cellulose, carbomer, cetostearyl alcohol, cetyl alcohol, glycol, glycerin, D-mannitol, trehalose, benzyl benzoate, ethanol, trisaminomethane, cholesterol, triethanolamine, sodium carbonate, sodium citrate, sodium salicylate, sodium acetate, and mixtures thereof.

The solubilizers may be present from about 1 weight percent to about 80 weight percent of the total weight of the composition.

Chelating agents can be added to trap metals that find their way into the compositions during processing. Suitable chelating agents may include, but are not limited to, one or more of ethylenediaminetetraacetic acid (EDTA), ethylenediamine (EDA), diethylenetriamine (DETA), aminoethylethanolamine (AEEA).

The chelating agents can be present in an amount from about 0.01 weight percent to about 3 weight percent of the total weight of the composition.

Through selection and combination of excipients according to the invention, liquid diacerein compositions can be provided that exhibit improved or more desired performance with respect to drug concentration, dissolution, dispersion, stability, safety, emulsification, efficacy, flavor, patient compliance, and/or other pharmacokinetic, chemical and/or physical properties.

The invention is further illustrated by the following examples which are provided merely to be exemplary of the invention and do not limit the scope of the invention. Certain modifications and equivalents will be apparent to those skilled in the art and are intended to be included within the scope of the invention.

Example 1

TABLE 1

| S.N. | Ingredients | % Composition |
|---|---|---|
| 1 | Diacerein | 0.5-3.75% |
| 2 | Tween | 0.01-0.5% |
| 3 | Xanthan gum | 0.25-10% |
| 4 | Aspartame | 0.1-5% |
| 5 | Colloidal Silicon Dioxide | 0.1-5% |
| 6 | Sodium citrate | 0.01-1% |
| 7 | Flavours | 0.01-5% |
| 8 | Sucrose | q.s. |

Procedure: Tween was adsorbed on colloidal silicon dioxide. Flavours, sodium citrate and aspartame were triturated together and added geometrically to xanthan gum to form a blend. The blend was mixed with diacerein, which was further mixed with sucrose to form a mixture. This mixture was blended with colloidal silicon dioxide adsorbed on tween to form dry powder for suspension. On reconstitution of the dry powder with water, pH of the resulting suspension was in the range of 5-7.0.

Example 2

TABLE 2

| S.N. | Ingredients | % Composition |
|---|---|---|
| 1 | Diacerein | 0.5-3.75% |
| 2 | Poloxamer | 0.01-0.5% |
| 3 | Microcrystalline cellulose | 0.25-10% |
| 4 | Aspartame | 0.1-5% |
| 5 | Colloidal Silicon Dioxide | 0.1-5% |
| 6 | Sodium citrate | 0.01-1% |
| 7 | Sodium phosphate | 0.01-1% |
| 8 | Flavours | 0.01-5% |
| 9 | Sucrose | q.s. |

Procedure: Poloxamer was adsorbed on colloidal silicon dioxide. Flavours, sodium citrate, sodium phosphate and aspartame were triturated together and added geometrically to microcrystalline cellulose to form a blend. The blend was mixed with diacerein, which was further mixed with sucrose to form a mixture. This mixture was blended with colloidal silicon dioxide adsorbed on poloxamer to form dry powder for suspension. On reconstitution of dry powder with water, pH of the resulting suspension was in the range of 5-7.0.

Example 3

TABLE 3

| S.N. | Ingredients | % Composition |
|---|---|---|
| 1 | Diacerein | 0.5-3.75% |
| 2 | Tween | 0.01-0.5% |
| 3 | Sodium carboxymethylcellulose | 0.25-10% |
| 4 | Sucralose | 0.1-5% |
| 5 | Colloidal Silicon Dioxide | 0.1-5% |
| 6 | Sodium citrate | 0.01-1% |
| 7 | Flavours | 0.01-5% |
| 8 | Sucrose | q.s. |

Procedure: Tween was adsorbed on colloidal silicon dioxide. Flavours, sodium citrate and sucralose were triturated together and added geometrically to sodium carboxymethyl cellulose to form a blend. The blend was mixed with diacerein, which was further mixed with sucrose to form a mixture. This mixture was blended with colloidal silicon dioxide adsorbed on tween to form dry powder for suspension. On reconstitution of dry powder with water, pH of the resulting suspension was in the range of 5-7.0.

Example 4

TABLE 4

| S.N. | Ingredients | % Composition |
|---|---|---|
| 1 | Diacerein | 0.5-3.75% |
| 2 | Poloxamer | 0.01-0.5% |
| 3 | Magnesium aluminium silicate | 0.25-10% |
| 4 | Acesulfame | 0.1-5% |
| 5 | Colloidal Silicon Dioxide | 0.1-5% |
| 6 | Sodium benzoate | 0.01-1% |
| 7 | Sodium citrate | 0.01-1% |
| 8 | Flavours | 0.01-5% |
| 9 | Sucrose | q.s. |

Procedure: Poloxamer was adsorbed on colloidal silicon dioxide. Flavours, sodium citrate, sodium benzoate and acesulfame were triturated together and added geometrically to magnesium aluminium silicate to form a blend. The blend was mixed with diacerein, which was further mixed with sucrose to form a mixture. This mixture was blended with colloidal silicon dioxide with adsorbed poloxamer to form dry powder for suspension. On reconstitution of dry powder with water, pH of the resulting suspension was in the range of 5-7.0.

Example 5

TABLE 5

| S.N. | Ingredients | % Composition |
|---|---|---|
| 1 | Diacerein | 0.5-3.75% |
| 2 | Poly vinyl pyrrolidone | 0.05-8.0% |
| 3 | Docusate sodium | 0.001-0.5% |
| 4 | Mannitol | 0.1-30% |
| 5 | Sucrose | 1.0-95.0% |
| 6 | Colloidal silicon dioxide | 0.01-5% |
| 7 | Sodium Benzoate | 0.001-0.5% |
| 8 | Sodium citrate | 0.001-0.5% |
| 9 | Xanthan gum | 0.1-10% |
| 10 | Sweetener | 0.001-1.0% |
| 11 | Flavoring agent | 0.001-1.0% |
| 12 | Water | q.s. |

Procedure: Docusate Sodium was dissolved in water to form a solution and poly vinyl pyrrolidone was added to it. Diacerein was added to the above solution to form dispersion. The dispersion was passed through a mill to form nano-sized dispersion. The nano-sized dispersion was sprayed on to mannitol to form dry granules. The dry granules were blended with sucrose, colloidal silicon dioxide, sodium citrate, sodium benzoate, xanthan gum, sweetener and flavor. The pH of the resulting suspension was in the range of 5-7.0.

TABLE 6

Dissolution profile of Diacerein suspension as per example 5.

| Time (minutes) | % Drug released |
|---|---|
| 15 | 48 |
| 30 | 79 |
| 45 | 92 |
| 60 | 100 |

Table 6 provides the dissolution data for diacerein suspension prepared as per the formula given in Table 5. For determination of drug release rate, USP Type 2 Apparatus (rpm 75) was used, wherein 1000 ml of pH 5.7 phosphate buffer at 37° C.±0.5° C. was used as a medium.

Example 6

TABLE 7

| S.N. | Ingredients | % Composition |
|---|---|---|
| 1 | Diacerein | 0.5-3.75% |
| 2 | Tween | 0.01-0.5% |
| 3 | Sucrose | 1.0-95.0% |
| 4 | Colloidal silicon dioxide | 0.01-5% |
| 5 | Sodium Benzoate | 0.001-0.5% |
| 6 | Sodium citrate | 0.001-0.5% |
| 7 | Microcrystalline cellulose | 0.01-5% |
| 8 | Flavours | 0.01-5% |
| 9 | Sucrose | q.s. |

Procedure: Tween was adsorbed on sucrose. Diacerein, colloidal silicon dioxide, sodium benzoate, sodium citrate, microcrystalline cellulose, sweetener and flavor were mixed with sucrose with adsorbed tween to form dry powder for suspension.

TABLE 8

Dissolution profile of composition of diacerein dry powder for suspension as per example 6.

| Time (minutes) | % Drug released |
|---|---|
| 15 | 46 |
| 30 | 75 |
| 45 | 89 |
| 60 | 100 |

Table 8 provides the dissolution data for diacerein dry powder for suspension prepared as per the formula given in Table 7. For determination of drug release rate, USP Type 2 Apparatus (rpm 75) was used, wherein 1000 ml of pH 5.7 phosphate buffer at 37° C.±0.5° C. was used as a medium.

While the invention has been described in terms of its specific embodiments, certain modifications and equivalents will be apparent to those skilled in the art and are intended to be included within the scope of the invention.

We claim:

1. A pharmaceutical composition in the form of dry syrups or solid ready mix comprising:

| Sr. No. | Ingredients | % Composition |
|---|---|---|
| 1. | Diacerein | 0.5-3.75% |
| 2. | Poloxamer | 0.01-0.5% |
| 3. | Magnesium aluminium silicate | 0.25-10% |
| 4. | Acesulfame | 0.1-5% |

-continued

| Sr. No. | Ingredients | % Composition |
|---|---|---|
| 5. | Colloidal silicon dioxide | 0.1-5% |
| 6. | Sodium benzoate | 0.01-15 |
| 7. | Sodium citrate | 0.01-1% |
| 8. | Flavours | 0.01-5% |
| 9. | Sucrose | q.s, | wherein said composition exhibits a dissolution profile such that more than 75% of diacerein is released within 30 minutes, wherein the release profile is measured in Apparatus 2 (USP, Dissolution, paddle, 75 rpm) using 1000 ml of pH 5.7 phosphate buffer at 37° C.±0.5° C.; and, wherein said composition results in a reduction of undesirable effects of soft stools.

2. A pharmaceutical composition in the form of dry syrups or solid ready mix comprising:

| Sr. No. | Ingredients | % Composition |
|---|---|---|
| 1. | Diacerein | 0.5-3.75% |
| 2. | Poly vinyl pyrrolidone | 0.05-8.0% |
| 3. | Docusate sodium | 0.001-0.5% |
| 4. | Mannitol | 0.1-30% |
| 5. | Sucrose | 1.0-95.0% |
| 6. | Colloidal silicon dioxide | 0.01-5% |
| 7. | Sodium benzoate | 0.001-0.5% |
| 8. | Sodium citrate | 0.001-0.5% |
| 9. | Xanthan gum | 0.1-10% |
| 10. | Sweetener | 0.001-1.0% |
| 11. | Flavoring agent | 0.001-1.0%, | wherein said composition exhibits a dissolution profile such that more than 75% of diacerein is released within 30 minutes, wherein the release profile is measured in Apparatus 2 (USP, Dissolution, paddle, 75 rpm) using 1000 ml of pH 5.7 phosphate buffer at 37° C.±0.5° C.; and, wherein said composition results in a reduction of undesirable effects of soft stools.

3. A pharmaceutical composition in the form of dry syrups or solid ready mix comprising:

| Sr. No. | Ingredients | % Composition |
|---|---|---|
| 1. | Diacerein | 0.5-3.75% |
| 2. | Polysorbate | 0.01-0.5% |
| 3. | Sucrose | 1.0-95.0% |
| 4. | Colloidal silicon dioxide | 0.01-5% |
| 5. | Sodium benzoate | 0.001-0.5% |
| 6. | Sodium citrate | 0.001-0.5% |
| 7. | Microcrystalline cellulose | 0.01-0.5% |
| 8. | Flavours | 0.01-0.5% |
| 9. | Sucrose | q.s, | wherein said composition exhibits a dissolution profile such that more than 75% of diacerein is released within 30 minutes, wherein the release profile is measured in Apparatus 2 (USP, Dissolution, paddle, 75 rpm) using 1000 ml of pH 5.7 phosphate buffer at 37° C.±0.5° C.; and, wherein said composition results in a reduction of undesirable effects of soft stools.

4. A pharmaceutical composition in the form of dry syrups or solid ready mix comprising:

| Sr. No. | Ingredients | % Composition |
|---|---|---|
| 1 | Diacerein | 0.5-3.75% |
| 2 | Polysorbate | 0.01-0.5% |
| 3 | Xanthan Gum | 0.25-10% |
| 4 | Aspartame | 0.1-5% |
| 5 | Colloidal Silicon dioxide | 0.1-5% |
| 6 | Sodium Citrate | 0.01-1% |
| 7 | Flavours | 0.01-5% |
| 8 | Sucrose | q.s., | wherein said composition exhibits a dissolution profile such that more than 75% of diacerein is released within 30 minutes, wherein the release profile is measured in Apparatus 2 (USP, Dissolution, paddle, 75 rpm) using 1000 ml of pH 5.7 phosphate buffer at 37° C.±0.5° C.; and, wherein said composition results in a reduction of undesirable effects of soft stools.

5. A pharmaceutical composition in the form of dry syrups or solid ready mix comprising:

| Sr. No. | Ingredients | % Composition |
|---|---|---|
| 1. | Diacerein | 0.5-3.75% |
| 2. | Poloxamer | 0.01-0.5% |
| 3. | Microcrystalline cellulose | 0.25-10% |
| 4. | Aspartame | 0.01-5% |
| 5. | Colloidal silicon dioxide | 0.1-5% |
| 6. | Sodium citrate | 0.01-1% |
| 7. | Sodium Phosphate | 0.01-1% |
| 8. | Flavours | 0.01-5% |
| 9. | Sucrose | q.s, | wherein said composition exhibits a dissolution profile such that more than 75% of diacerein is released within 30 minutes, wherein the release profile is measured in Apparatus 2 (USP, Dissolution, paddle, 75 rpm) using 1000 ml of pH 5.7 phosphate buffer at 37° C.±0.5° C.; and, wherein said composition results in a reduction of undesirable effects of soft stools.

6. A pharmaceutical composition in the form of dry syrups or solid ready mix comprising:

| Sr. No. | Ingredients | % Composition |
|---|---|---|
| 1 | Diacerein | 0.5-3.75% |
| 2 | Polysorbate | 0.01-0.5% |
| 3 | Sodium carboxymethyl cellulose | 0.25-10% |
| 4 | Sucralose | 0.1-5% |
| 5 | Colloidal Silicon dioxide | 0.1-5% |
| 6 | Sodium Citrate | 0.01-1% |
| 7 | Flavours | 0.01-5% |
| 8 | Sucrose | q.s., | wherein said composition exhibits a dissolution profile such that more than 75% of diacerein is released within 30 minutes, wherein the release profile is measured in Apparatus 2 (USP, Dissolution, paddle, 75 rpm) using 1000 ml of pH 5.7 phosphate buffer at 37° C.±0.5° C.; and, wherein said composition results in a reduction of undesirable effects of soft stools.

\* \* \* \* \*